ns Patent [19] [11] 3,971,948
Pfeiler et al. [45] July 27, 1976

[54] X-RAY DIAGNOSTIC APPARATUS FOR PRODUCING A TRANSVERSE LAYER IMAGE

[75] Inventors: Manfred Pfeiler, Erlangen; Gerhard Linke, Erlangen-Frauenaurach, both of Germany

[73] Assignee: Siemens Aktiengesellschaft, Erlangen, Germany

[22] Filed: Aug. 2, 1974

[21] Appl. No.: 494,272

[30] Foreign Application Priority Data
Aug. 6, 1973 Germany............................ 2339758

[52] U.S. Cl. ............................ 250/445 T; 250/366; 250/492 R
[51] Int. Cl.² ........................................ G01M 23/00
[58] Field of Search ........ 250/362, 363, 366, 445 T, 250/494, 492

[56] References Cited
UNITED STATES PATENTS
| | | | |
|---|---|---|---|
| 3,777,144 | 12/1973 | Rapkin et al. ...................... | 250/366 |
| 3,778,614 | 12/1973 | Hounsfield .......................... | 250/366 |

Primary Examiner—Alfred E. Smith
Assistant Examiner—B. C. Anderson
Attorney, Agent, or Firm—Haseltine, Lake & Waters

[57] ABSTRACT

An X-ray diagnostic installation for producing a transverse layer or planigraphic image including a first X-ray measuring arrangement having X-ray source which generates an X-ray beam whose extent of cross-sectional diffusion perpendicular to the layer is equal to the layer thickness, and equal to or less than the layer thickness in parallel to the layer, and a radiation receiver which measures the radiation intensity behind the object at successive equidistantly located points, as well as a drive arrangement for the measuring arrangement adapted to generate a linearly guided scanning motion extending in perpendicular to the direction of the central beam across the total expanse of the object, in an alternating sequence with a rotational motion about small equidistant angles, whose sum comprises 180°, and about a center of revolution lying approximately in the central portion of the layer surface on the main radiation beam. In addition to the first measuring arrangement, a second measuring arrangement is provided which is parallel offset with respect to the former in the direction of the linear movement, whose X-ray source generates radiation having a different value of radiation energy in comparison with that of the first X-ray source; and including a calculator which determines for each image point from the measuring signals of both measuring arrangements for the two different values the radiation energy, the two adsorption coefficients or their proportional magnitudes, forms their respective quotients and from the foregoing, by means of a computed-in calibrating table provides the median ordinate value or a corresponding magnitude for each image point.

3 Claims, 2 Drawing Figures

X-RAY DIAGNOSTIC APPARATUS FOR PRODUCING A TRANSVERSE LAYER IMAGE

FIELD OF THE INVENTION

The present invention relates to an X-ray diagnostic installation for producing a transverse layer or planigraphic picture.

The installation consists of an X-ray measuring arrangement having X-ray source which generates an X-ray beam whose extent of cross-sectional diffusion perpendicular to the layer is equal to the layer thickness, and equal to or less than the layer thickness in parallel to the layer; and a radiation receiver which measures the radiation intensity behind the object at successive equidistantly located points, as well as a drive arrangement for the measuring arrangement adapted to generate a linearly guided scanning motion extending in perpendicular to the direction of the central beam across the total expanse of the object, in an alternating sequence with a rotational motion about small equidistant angles whose sum comprises 180°, and about a center of revolution lying approximately in the central portion of the layer surface on the main radiation beam.

DISCUSSION OF THE PRIOR ART

An installation of the above-mentioned type is known under the designation "EMI-scanner" and the examining method carried out therewith as "Computer-Tomography", as described in the journal "ELECTRONICS TODAY INTERNATIONAL", August 1972, pages 16 through 19, under the heading "Breakthrough in brain X-ray". This transverse layer or planigraphic method is vastly superior to all previous methods of this type with regard to the formation of object details which have the minutest contrast distinctions. Thus, for example, it facilitates the distinguishing between white and gray brain substance without the need for addition of X-ray contrasting media although both substances, at the usual exposure voltages, distinguish only at about 1 to 2% within the absorptive capacity for X-rays. The previously known transverse layer method, in whose simplist embodiment the patient and the film are synchronously rotated about mutually parallel axes, and wherein the central beam extends through the pivoting point of the film and the rotational axis of the patient, and contacts the film at an angle of incidence of between 60° and 75° is, by far, not in a position to reproduce images at such low degrees of absorptive distinctions. More frequently it delivers exposures, in which the image of the instantaneously set layer are superimposed with the slurred image of the object regions externally of this layer which are located within the cone of the X-ray beam. This superposition has a result in that only those object details can be ascertained, whose X-ray adsorptive capacity for X-rays distinguish by at least about 20%. In comparison therewith, the Computer-Tomography method delivers a transverse layer of planigraphic picture, in whose formation there is processed only information from the layer of interest per se is utilized, and in which the previously mentioned superpositions of adjacent regions are eliminated.

The function of the process may, in short, be described in the following manner:

It is assumed that the layer is assembled or constructed of $n \times n$ small squares each having the size $b \times b \times d$, wherein $b$ is the edge length of the square extending parallel to plane of the layer, $d$ is the thickness of the layer, and $n$ a whole number whose order of magnitude is about 100. The corresponding cross-layer picture thus forms a matrix of $n \times n$ square image points. The magnitude which defines the X-ray adsorptive capacity for the particular object material which in the simplest case, is also the prevailing coefficient of absorption, is to be obtained for each individual image point. The measured value for the finding of this $n^2$ unknown is achieved in the following manner:

The exposed object is linearly scanned by means of a fine X-ray beam extending within the layer at various projections. A radiation receiver may be employed, which consists of a scintillation crystal with a photomultiplier connected thereto. The radiation intensity behind the exposed object is measured during the linear scanning sequence (hereinafter referred to shortly as "scan") at equidistant points, and then converted into digital values with the aid of a suitable converter, which are stored in a computer. After each scan there is carried out a rotation of the entire scanning system about a rotational axis which approximately coincides with the longitudinal axis of the exposed object perpendicular to the layer about a small fixedly selected angular amount of, for example 1°. This sequence is repeated for so long, until the total extent of rotation of the system constitutes 180°. The measuremenets which are carried through in this manner provide a linear equation system of $n \times w$ equations with $n^2$ unknowns, in which $w$ defines the number of angular steps.

A direct solution of this equation system in accordance with the unknown median absorption coefficients for all image points with the aid of the usual matrix operation is above all, not possible due to the magnitude of the matrix. A solution may, however, be found in an iterative manner with the aid of a calculator.

The representation of the transverse layer image obtained through the calculator may be achieved in various ways. The simplest possibility consists of in reproducing the obtained digital values by means of a high-speed printer which is connected to the calculator, wherein the values may be suitably correlated with the associated matrix elements. The evaluation of such an image is, however, rather cumbersome and unfamiliar to the practitioner. It is much easier to convert the obtained values into analog signals, and to reproduce them on a video monitor or screen as the gray steps in a matrix arrangement. This provides for the physician a trustworthy video picture which closely approximates the X-ray exposure, and whose evaluation becomes quite simple. In addition thereto, through video reproduction there is provided the possibility of further enhancing contrasts through electronic means.

From the results of the previously described means, there may thus be obtained information with respect to X-ray adsorption, in effect meaning, about the product from the specific adsorption coefficient and the thickness of the object material within the individual matrix elements; however, since the thickness of the particular material is generally not known, no information can be obtained with respect to the median arrangement or, respectively, the chemical composition of the materials.

SUMMARY OF THE INVENTION

Accordingly, it is an object of the present invention to provide the possibility, with the assistance of the abovedescribed installation, to obtain information with regard to the material itself within the individual matrix elements.

This object of the invention is inventively achieved in that there is provided, in addition to a first measuring arrangement, a second measuring arrangement which is parallel offset with respect to the former in the direction of the linear movement, whose X-ray source generates radiation having a different value of radiation energy in comparison with that of the first X-ray source; and including a calculator which determines for each image point from the measuring signals of both measuring arrangements for the two different values the radiation energy, the two adsorption coefficients or their proportional magnitudes, forms their respective quotients and from the foregoing, by means of a computed-in calibrating table provides the median ordinate value or a corresponding magnitude for each image point. In this manner, for a skeleton diagnosis there may, for example, be ascertained the particularly important calcium content or various, eventually concurrently applied contrast means may be distinguished from each other.

BRIEF DESCRIPTION OF THE DRAWING

The invention is now described in detail with respect to the following exemplary embodiment thereof, taken in conjunction with the accompanying drawing; in which.

DETAILED DESCRIPTION

Figure 1:
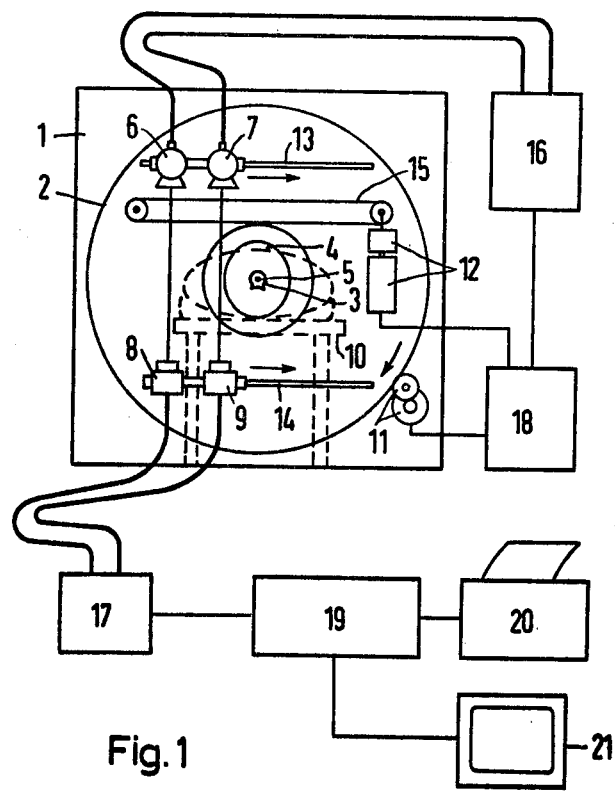
FIG. 1 shows a basic diagrammatic illustration of an X-ray diagnostic installation according to the present invention.

Referring now in detail to FIG. 1 of the drawing, in the installation illustrated therein, a carrier ring 2, which is rotatably supported on a frame portion 1, moves about a rotational axis 5 which generally coincides with the body trunk portion 3 of a patient 4. Located on the carrier ring 2 are two identical X-ray measuring arrangements, consisting of X-ray tubes 6 and 7, and radiation receivers 8 and 9, which are displaced in parallel along the direction of their linear movement. The rotational movement of the carrier ring 2 about the X-rayed body portion of the patient 4 resting on the support bed 10 is carried out by means of a drive arrangement 11. A further drive arrangement 12 serves to effect the linear scan movement of the mutually interconnected measuring arrangement 6, 7, 8 and 9 which move on rails 13 and 14. Both of the X-ray tubes 6 and 7 are electrically connected with an X-ray generator 16 which supplies them with high constant electrical voltage of varied height. The drive arrangements 11 and 12 for, respectively, the circular and linear movements are connected with a control arrangement 18, which coordinates both movements in their alternating sequence and the operative cycle of the X-ray tubes 6 and 7 with regard to each other. The radiation receivers are connected with a computer 19 through a matching connection 17. The output of the data which is calculated by the computer is provided by a teletype printer 20 and a video apparatus 21.

Figure 2:
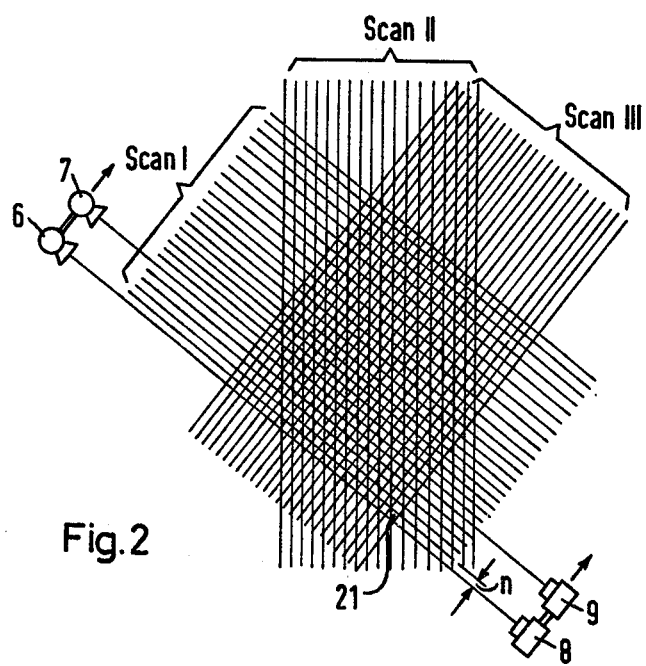
FIG. 2 shows a scanning schematic diagram employed for obtaining the layer image.

In the following description, the function of the installation of FIGS. 1 and 2 is explained in closer detail: After switching on, the drive arrangement 11 is actuated so as to move the carrier ring 2 into an outlet position which is offset with respect to the illustrated position by about 90°. Upon attainment of this position, scanning is commenced in a manner whereby the drive arrangement 12 displaces the measuring arrangements 6, 7, 8 and 9 in the linear scan movement in which the desired transverse layer of the patient 4 is X-ray and concurrently scanned (Scan I). For this purpose, first the X-ray tube 7, and then the X-ray tube 6, are actuated upon reaching the region which is to be X-rayed, and the measuring signal of the radiation receiver 9 and, respectively, 8 in equidistant intervals which correspond to the desired edge length of an image point 21 (matrix elements), are received and stored by the computer 19 through the matching connector 17. As soon as the X-ray tube 7 has left the region which is to be X-rayed, it is switched off, and receipt of the measuring signal of the radiation receiver 9 in the storage of the computer is terminated. Similarly, as soon as the X-ray tube 6 has left the region which is to be X-rayed it is also switched off, and receipt of the measuring signal of the radiation receiver 8 in the storage of the computer is also terminated, and finally the drive arrangement 12 is deactivated. Thereby, Scan I is completed. Subsequently, the measuring arrangement is reconveyed into its starting operating position. Concurrently, the drive arrangement 21 is actuated for so long until the carrier ring 2 is conveyed further about the desired angle (approximately 1°). A new scanning sequence (Scan II) is then carried out, which is analogous to the previously described Scan I. Subseqently, the carrier ring is again rotated about the same angular displacement and the further Scan III is carried out. This sequence is repeated for so long, until the carrier ring has completed a total rotation of 180°. Naturally, it is also possible to forego the reconveyance of the measuring arrangement after each scan, and in lieu thereof to meanderingly scan the object.

After completion of the scanning sequence, there are then present in the computer two linear equation system of each $n \times w$ equations each with $n^2$, wherein $n$ designates the number of matrix points, $m$ the number of measured values for each scan, and $w$ the number of scans. The calculator next determines for each matrix point from these two equation systems the two adsorption coefficients for the two different values of the radiation energy, then forms the respective quotients from the two adsorption coefficients, and finally provides, with the aid of a stored-in calibrating table, the corresponding median ordinate value for each matrix element. The thus obtaned values for the median ordinates appear then on the teletype printer 20 as digital values, as well as in an analogous form as gray values on the video apparatus 21.

While there has been shown what is considered to be the preferred embodiment of the invention, it will be obvious that modifications may be made which come within the scope of the disclosure of the specification.

What is claimed is:

1. In an X-ray diagnostic apparatus for producing a transverse-layer image; including a first X-ray measuring arrangement having an X-ray source generating an X-ray of a transverse diffusion perpendicular to the layer being equal to the layer thickness and parallel to the layer being equal to or lesser than the layer thickness, a first radiation receiver means in said arrangement for measuring the radiation intensity behind an object at successive equidistant points, and drive means for said measuring arrangement for effecting a linear scanning movement across the entire object expanse perpendicular to the direction of the central X-ray in alternating sequence at small equidistant angular increments over a range of 180°, said angular increments being measured about a rotational point on said central X-ray approximately centrally of said layer plane, the improvement comprising; a second measuring arrangement being disposed in parallel offset relationship with respect to the linear direction of movement of said first measuring arrangement including an X-ray source generating X-rays of different radiation energy value in comparison with the x-rays of the X-ray source of said first measuring arrangement, a second radiation receiver means in said arrangement for measuring the radiation intensity behind the object at successive equidistant points for receiving the X-rays of different radiation value; a calculator for formulating two absorption coefficients or their proportional magnitudes for each image point in dependence upon the measured signals of said first and second measuring arrangements for the two different values of the radiation energy, said calculator being adapted to form respective quotients and through stored calibrating tables provide the median ordinate value or corresponding parameter for each image point.

2. An apparatus as claimed in claim 1, said measuring arrangement being through incremental successive angular displacements each comprising about 1°.

3. An apparatus as claimed in claim 1, said first and second measuring arrangements being of substantially identical constructions.

* * * * *